US00PP32160P2

(12) United States Plant Patent
Bradford et al.

(10) Patent No.: US PP32,160 P2
(45) Date of Patent: Sep. 8, 2020

(54) PLUM TREE NAMED 'PLUMCANDY XVII'

(50) Latin Name: *Prunus salicina*
Varietal Denomination: PLUMCANDY XVII

(71) Applicants: Lowell Glen Bradford, Le Grand, CA (US); Jon M. Quisenberry, Le Grand, CA (US)

(72) Inventors: Lowell Glen Bradford, Le Grand, CA (US); Jon M. Quisenberry, Le Grand, CA (US)

( * ) Notice: Subject to any disclaimer, the term of this patent is extended or adjusted under 35 U.S.C. 154(b) by 0 days.

(21) Appl. No.: 16/602,917

(22) Filed: Dec. 23, 2019

(51) Int. Cl.
*A01H 5/08* (2018.01)
*A01H 6/74* (2018.01)

(52) U.S. Cl.
USPC ..... Plt./184

(58) Field of Classification Search
USPC ..... Plt./156, 180, 184
See application file for complete search history.

(56) References Cited

U.S. PATENT DOCUMENTS

PP28,400 P3 9/2017 Bradford
PP28,468 P3 10/2017 Bradford

*Primary Examiner* — Susan McCormick Ewoldt
*Assistant Examiner* — Karen M Redden

(57) ABSTRACT

The present invention relates to a plum tree and more particularly to a new and distinct variety broadly characterized by a small size, moderately vigorous, hardy, and very productive tree. Being self-unfruitful, the present variety requires cross pollination from an apricot, interspecific, or plum that blooms during the mid season, such as 'Plumcandy XIII' plum tree (U.S. Plant Pat. No. 28,468). The fruit matures under the ecological conditions described during the last part of September, with first picking on Sep. 29, 2019, and will hang on the tree an additional thirty days. The fruit is uniformly medium to large in size, very dark red in skin color, orange yellow to dark red in flesh color, clingstone in type, slightly oblate in shape, firm in texture, very sweet, and excellent in flavor.

1 Drawing Sheet

Botanical classification: *Prunus salicina.*
Varietal denomination: 'PLUMCANDY XVII'.

BACKGROUND OF THE VARIETY

In a continuing effort to improve the quality of shipping fruits, we, the inventors, typically hybridize a large number of peach, nectarine, plum, apricot, and cherry seedlings each year. We also grow a lesser number of open pollinated seeds of each of these fruits. The present invention relates to a new and distinct variety of plum tree, which has been denominated varietally as 'PLUMCANDY XVII'.

During 2013 we gathered fruit from several different late maturing plum trees that were located on our ranch in Le Grand, Calif. The seeds were removed, cracked, stratified and germinated as a group with the label "LATE PLUM BAGS". They were grown as seedlings on their own root in our greenhouse and upon reaching dormancy transplanted to a cultivated area of our experimental orchard located near Le Grand, Calif. in Merced County (San Joaquin Valley). During the spring of 2016 the claimed variety was selected by us as a single plant from the group of seedlings described above. Subsequent to the origination of the present variety of plum tree, we asexually reproduced it by budding and grafting in the experimental orchard described above, and such reproductions were true to the original tree in all respects. The reproduction of the variety included the use of 'Nemaguard' (unpatented) rootstock upon which the present variety was compatible and true to type.

The present variety is most similar to 'Plumred XII' plum tree (U.S. Plant Pat. No. 28,400) by being self-unfruitful, by blooming in the mid to late season, and by producing fruit that is somewhat oblate in shape, mostly red in flesh color, firm in texture, and very sweet in flavor, but is distinguished therefrom by having a smaller size tree and by producing fruit that is somewhat larger in size, darker red in skin color, clingstone instead of semi-freestone in type, and that matures about ten days later.

SUMMARY OF VARIETY

The present plum variety is characterized by a small size, moderately vigorous, hardy, and very productive tree. Being self-unfruitful, the present variety requires cross pollination from an apricot, interspecific, or plum that blooms during the mid season, such as 'Plumcandy XIII' plum tree (U.S. Plant Pat. No. 28,468). The present variety produces a moderate amount of blossoms with a strong amount of pollen to entice good bee activity to facilitate pollination. The fruit matures under the ecological conditions described during the last part of September, with first picking on Sep. 29, 2019, and will hang on the tree an additional thirty days. The fruit is uniformly medium to large in size, very dark red in skin color, orange yellow to dark red in flesh color, clingstone in type, slightly oblate in shape, firm in texture, very sweet, and excellent in flavor.

DRAWING

The accompanying photograph consists of four whole fruits positioned to display the characteristics of the skin color and form, one divided fruit to reveal the flesh and stone, typical leaves, and two insets depicting the flower buds and blossoms as they appeared on the tree during the blooming season.

POMOLOGICAL CHARACTERISTICS

Referring now more specifically to the pomological characteristics of this new and distinct variety of plum tree, the following has been observed under the ecological conditions prevailing near Le Grand, Merced County (San Joaquin Valley), Calif. The fruit description was developed at the state of full ripe on Oct. 16, 2019, on the original tree during its sixth growing season. The flower and bud descriptions were developed during the previous blooming season. All major color code designations are by reference to the Inter-Society Color Council, National Bureau of Standards. Common color names are also used occasionally.

PARENTAGE

Seed parent: Unknown.
Pollen parent: Unknown.

TREE

Size: Small, reaching a height of 8' [2.44 m.] and a spread of 6' [1.83 m.] after six growing seasons utilizing typical dormant pruning.

Vigor: Moderately vigorous, responding about average to irrigation and fertilization. The variety grows about 2' [0.61 m.] of surplus top-growth during the spring and summer. The plant should be grown on a standard commercial rootstock for production purposes.

Growth: Upright.

Form: Pruned to a central leader type.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Very productive, thinning usually necessary.

Fertility: Self-unfruitful, requiring cross pollination by a suitable mid to late seasonal blooming apricot, interspecific, or plum, such as 'Plumcandy XIII' (U.S. Plant Pat. No. 28,468) plum tree.

Bearing: Regular bearer, weather dependent, with no crop failures observed as of yet.

Leaf bud burst: Medium, toward the middle of flowering.

Trunk:

- *Size*.—Medium, reaching a maximum diameter of 2½" [63.5 mm.] after the sixth growing season.
- *Texture*.—Medium.
- *Bark color*.—A Grayish yellowish brown [80. gy.yBr] and Dark grayish brown [62. d.gy.Br] variegation with Moderate yellowish brown [77. m.yBr] crevices present.
- *Lenticels*.—Approximate Number Per Square Inch: 14. Color: Deep orange [51. deep 0]. Average Size: ¼" [6.4 mm.] in length. The width is typically one fourth as much as the length. Shape: Elongated.

Branches:

- *Size*.—Medium, diameter of the scaffold is 1¾" [44.5 mm.] measured 12" above the lowest hanger, the maximum diameter of the lowest hanger is 1" [25.4 mm.].
- *Texture*.—Smooth on first and second year wood, increasing in roughness with age.
- *Color*.—1st Year Wood Topside: Grayish red [19. gy.R]. 1st Year Wood Underside: Brilliant yellow green [116. brill.YG]. 2nd Year Wood: A Brownish gray [64. brGy] with Grayish brown [61. gy.Br] variegation.
- *Lenticels*.—Number Per Square Inch: About 20. Color: Strong yellowish brown [74. s.yBr]. Average Size: Small, 1/32" [0.8 mm.] in length. The width is typically one fourth as much as the length. Shape: Elongated.

Leaves:

- *Size*.—Medium.
- *Average length*.—3⅝" [92.1 mm.].
- *Average width:* 1 9/16" [39.7 mm.].
- *Arrangement*.—Alternate.
- *Thickness*.—Medium.
- *Form*.—Elliptical.
- *Apex*.—Acuminate.
- *Base*.—Acute with an average base angle of 75 degrees.
- *Surface*.—Smooth on both sides.
- *Color*.—Dorsal Surface: Moderate olive green [125. m.OlG]. Ventral Surface: Moderate yellow green [120. m.YG].
- *Red midvein*.—Absent.
- *Margin*.—Finely serrate.
- *Venation*.—Pinnately net veined.
- *Petiole*.—Average Length: ½" [12.7 mm.]. Average Thickness: 1/16" [1.6 mm.]. Color: Deep reddish orange [36. deep rO].
- *Stipules*.—Number: Usually 2 per leaf, up to 6 per growing tip. Average Length: ¼" [6.4 mm.]. Color: Pale yellow [89. p.Y] becoming Moderate reddish brown [43. m.rBr] with age.
- *Glands*.—Number: Usually 1 to 2 per leaf. Position: Usually alternate, positioned near the intersection of the petiole and the leaf blade. Form: Globose. Size: Medium, 1/48" [0.5 mm.] in diameter. Color: Pale greenish yellow [104. p.gY] becoming Moderate reddish brown [43. m.rBr] with age. Leaf buds: Pointed.

Flower buds:

- *Hardiness*.—Hardy with respect to central California blooming season.
- *Diameter*.—Typically 3/16" [4.8 mm.] 1 week before bloom.
- *Length*.—Typically ⅜" [9.5 mm.] 1 week before bloom.
- *Form*.—Not appressed.
- *Surface*.—Very slightly pubescent.
- *Tip color*.—White [263. White].

Flowers: Perfect, complete, perigynous, usually a single pistil, typically thirty or more stamens, five sepals and petal locations alternately positioned.

- *Average flower diameter*.—1¼" [31.8 mm.].
- *Average flower depth*.—⅜" [9.5 mm.] when fully open.
- *Average pedicel length*.—⅜" [9.5 mm.].
- *Number of petals*.—Five, no double blossoms observed.
- *Petal arrangement*.—Slightly overlapping at full bloom.
- *Petal shape*.—Oval.
- *Petal margin*.—Entire, somewhat wavy.

*Average petal diameter.*—7/16" [11.1 mm.].
*Average petal length.*—9/16" [14.3 mm.].
*Petal apex.*—Rounded.
*Petal base.*—Obtuse.
*Petal color.*—White [263. White] on both sides.
*Anther color.*—Light orange yellow [70. l.OY].
*Pollen production.*—Strong, good enticement to bees.
*Pollen color.*—Brilliant yellow [83. brill.Y].
*Stigma color.*—Brilliant greenish yellow [98. brill.gY].
*Stigma position.*—Located slightly above the surrounding anthers.
*Ovary.*—Non-pubescent.
*Sepal color.*—Light yellow green [119. l.YG] on both sides.
*Sepal outer surface.*—Very slightly pubescent.
*Sepal length.*—3/16" [4.8 mm.].
*Sepal width.*—1/8" [3.2 mm.].
*Sepal apex.*—Rounded to elliptical to match the width and length.
*Sepal margin.*—Fairly smooth.
*Average pistil length.*—9/16" [14.3 mm.].
*Average stamen length.*—7/16" [11.1 mm.].
*Stamen position.*—Typically located about 1/32" [0.8 mm.] below the petals.
*Fragrance.*—Moderate.
*Bloom density.*—Moderate to heavy.
*Number per cluster.*—2 to 6.
*Blooming period.*—Medium to late, about five days after 'Santa Rosa' plum (unpatented).
*Onset of bloom.*—One percent on Feb. 27, 2019.
*Date of full bloom.*—Mar. 9, 2019.
*Duration of bloom.*—One to two weeks, dependent on ambient temperature.

FRUIT

Maturity when described: Full ripe, Oct. 16, 2019.
Date of first picking: Sep. 29, 2019.
Date of last picking: Oct. 23, 2019.
Size: Uniform, medium to large.
*Average diameter axially.*—2 9/16" [65.1 mm.].
*Average diameter across cheek plane.*—2 11/16" [68.3 mm.].
*Average diameter across suture plane.*—2 11/16" [68.3 mm.].
*Typical weight.*—7.1 ounces [201 grams].
Form: Uniform, slightly oblate, somewhat compressed axially, mostly symmetrical.
*Longitudinal section form.*—Slightly oblate.
*Transverse section through diameter.*—Round.
Suture: A shallow groove extending from the base just to the apex.
Ventral surface: Rounded, lipped on both sides.
Lips: Fairly equal.
Cavity: Flaring.
*Depth.*—5/8" [15.9 mm.].
*Breadth.*—1 1/8" [28.6 mm.].
*Stem markings.*—Occasional, Deep red [13. deep R].
Base: Somewhat truncate, slightly cordate if viewed parallel to the suture.
Apex: Rounded to slightly truncate.
Pistil point: An inconspicuous Pale yellow [89. p.Y] dot depressed within the suture.
Stem: Medium.
*Average length.*—7/16" [11.1 mm.].
*Average width.*—1/8" [3.2 mm.].
Skin:
*Thickness.*—Medium.
*Surface.*—Smooth.
*Tenacity.*—Tenacious to the flesh.
*Astringency.*—Moderate.
*Tendency to crack.*—None observed.
*Color.*—Very dark red [17. v.d.R] toward the shoulders smoothly blending into Dark red [16. d.R] toward the apex with heavy Light orange yellow [70. l.OY] freckling throughout.
*Lenticels.*—Number Per Square Inch: About 250. Average diameter: 1/100" [0.25 mm].
*Bloom.*—Moderate to heavy.
Flesh:
*Color.*—Vivid orange yellow [66. v.OY] blending into Deep red [13. deep R] toward both the skin and stone.
*Surface of pit cavity.*—Covered with Deep red [13. deep R] fibers when twisted away from the stone.
*Amygdalin.*—Moderate to scarce.
*Juice.*—Abundant.
*Texture.*—Firm and crisp.
*Fibers.*—Abundant, fine, tender.
*Ripens.*—Fairly evenly.
*Flavor.*—A tasty balance of acid and sugar, typically 21 brix.
*Aroma.*—Very slight.
*Eating quality.*—Excellent.

STONE

Type: Semi-freestone.
Form: Obovate.
Hilum: Narrow, oval.
Base: Truncate.
Apex: Rounded.
Sides: Fairly equal.
Surface: Fairly smooth with rounded ridges toward the base.
External color of stone: Brownish orange [54. brO] when first removed.
Pit wall color when cracked: Light orange yellow [70. l.OY].
Cavity surface color: Strong brown [55. s.Br].
Average pit wall thickness: 1/16" [1.6 mm.].
Average length: 7/8" [22.2 mm.].
Average width: 1/2" [12.7 mm.].
Average breadth: 3/8" [9.5 mm.].
Tendency to split: None observed.
Kernel:
*Form.*—Oval.
*Skin color.*—Dark orange yellow [72. d.OY].
*Pellicle color.*—Deep yellowish brown [75. deep yBr].
*Vein color.*—Moderate yellowish brown [77. m.yBr].
*Taste.*—Bitter.
*Viable.*—Yes.
*Average length.*—1/2" [12.7 mm.].
*Average width.*—3/8" [9.5 mm.].
*Amygdalin.*—Abundant.

USE

Market: Fresh market and long distance shipping.
Keeping quality: Good, fruit quality observed to remain in good condition after 21 days in standard cold room at 36° Fahrenheit [2° Celsius].

Shipping quality: Good.
Resistance to insects: Not tested.
Resistance to diseases: Not tested.

OTHER NOTES

Although the new variety of plum tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of plum tree, *Prunus salicina*, substantially as illustrated and described, that is most similar to 'Plumred XII' plum tree (U.S. Plant Pat. No. 28,400) by being self-unfruitful, by blooming in the mid to late season, and by producing fruit that is somewhat oblate in shape, mostly red in flesh color, firm in texture, and very sweet in flavor, but is distinguished therefrom by having a smaller size tree and by producing fruit that is somewhat larger in size, darker red in skin color, clingstone instead of semi-freestone in type, and that matures about ten days later.

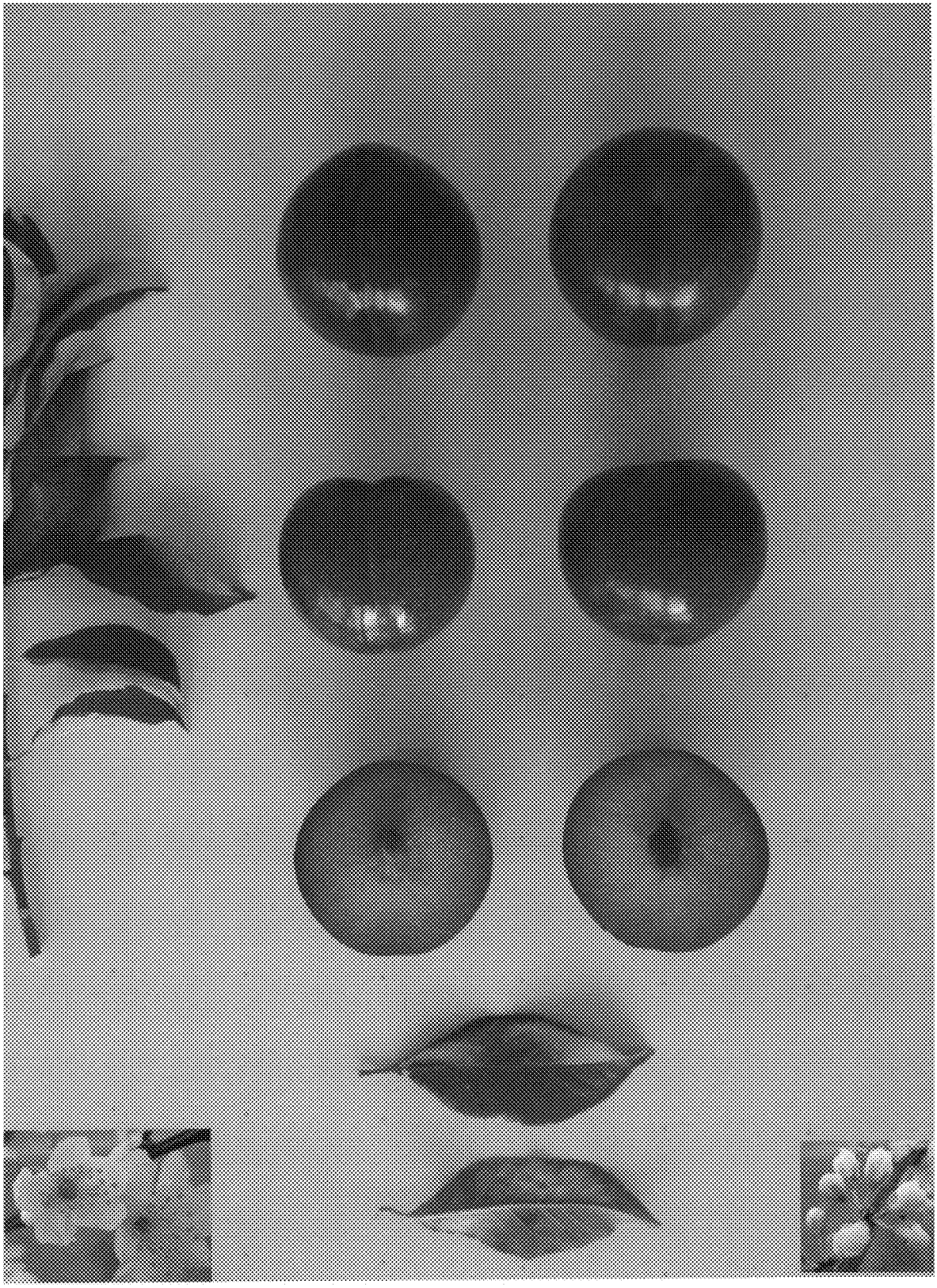

* * * * *